United States Patent [19]

Nashef et al.

[11] Patent Number: 4,776,349
[45] Date of Patent: Oct. 11, 1988

[54] TUBULAR DEVICE FOR THE TREATMENT OF HOLLOW ORGANS WITH ELECTRIC CURRENT

[76] Inventors: Basem Nashef, Geylinggasse 30, A-1130 Wien; Gerald Urban, Rembrandstrasse 19, A-1020 Wien; Werner Kovac, Mariahilferstrasse 127, A-1060; Helmuth Denck, Kirchmayergasse 5-7, Haus C, A-1130 Wien, all of Austria

[21] Appl. No.: 914,867

[22] Filed: Oct. 3, 1986

[30] Foreign Application Priority Data

Oct. 4, 1985 [AT] Austria .................................. 2881/85

[51] Int. Cl.⁴ .............................................. A61N 1/36
[52] U.S. Cl. .................................... 128/786; 128/784; 604/21; 604/101; 604/265
[58] Field of Search ................ 128/786, 303.17, 348.1; 604/21, 101, 265; 128/785, 794, 419 D

[56] References Cited

U.S. PATENT DOCUMENTS

| | | | |
|---|---|---|---|
| 3,837,347 | 9/1974 | Tower | 604/21 |
| 3,937,225 | 2/1976 | Schramm | 128/785 |
| 4,090,518 | 5/1978 | Elam | 128/696 |
| 4,304,239 | 12/1981 | Perlin | 128/786 |
| 4,442,841 | 4/1984 | Vehana et al. | 128/635 |
| 4,559,951 | 12/1985 | Dahl et al. | 128/642 |
| 4,574,807 | 3/1986 | Hewson et al. | 128/786 |
| 4,590,950 | 5/1986 | Iwaszkiewicz et al. | 128/786 |
| 4,640,983 | 2/1987 | Comte | 128/784 |
| 4,660,571 | 4/1987 | Hess et al. | 128/784 |
| 4,664,114 | 5/1987 | Ghodsian | 604/101 |
| 4,682,596 | 7/1987 | Bales et al. | 128/303.17 |

FOREIGN PATENT DOCUMENTS 0133400 1/1979 Fed. Rep. of Germany ...... 128/786
8200768 3/1982 PCT Int'l Appl. .

Primary Examiner—W. E. Kamm
Assistant Examiner—Timothy Keegan
Attorney, Agent, or Firm—Spensley Horn Jubas & Lubitz

[57] ABSTRACT

A tubular device for the treatment of hollow organs is flexibly arranged and comprises a coating of silver. This coating is connected to a current source via connecting wires. Particularly, the tubular device is used for the treatment of the esophagus, and by the irritation caused by the electric current it is to effect an inflammation of the esophagus wall and thus a thickening of the latter so as to reduce the danger of hemorraghes of varicose veins within the esophagus or to prevent the hemorraghes. The tubular device is expansible in order to secure a close abutment of the silver coating against the mucous membrane of the esophagus.

17 Claims, 1 Drawing Sheet

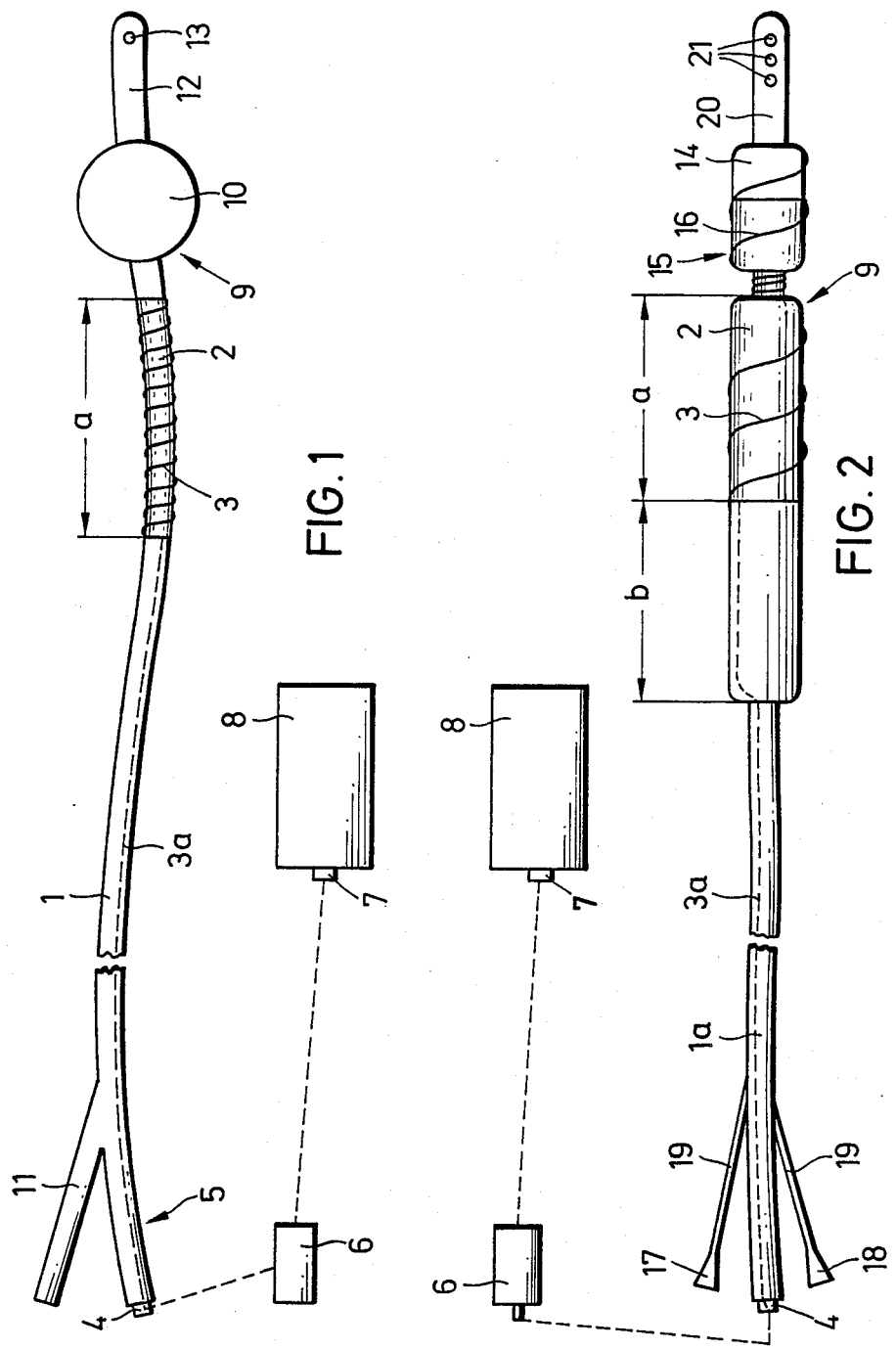

TUBULAR DEVICE FOR THE TREATMENT OF HOLLOW ORGANS WITH ELECTRIC CURRENT

It is especially in the gullet (oesophagus) that varicose veins occur sometimes, which varicose veins lead to hemorrhages. Such hemorrhages are often difficult to staunch and therefore represent an acute danger to life. The invention refers to a tubular device for the treatment of hollow organs including mucous membranes, in particular of the esophagus, with electric current, and especially for the treatment of varicose veins. There are known, for example, stiff probes of silver sheet for the treatment of the esophagus. These probes are introduced into the esophagus, and under the influence of electric current a thrombosing of the varicose veins is caused. By this thickening of the mucous membrane, the varicose veins are protected, and thus hemorrhages are prevented. To this purpose, however, the tubular member must closely abut against the mucous membrane, because otherwise a current transmitting is not possible and furthermore, there is the danger of injuries. Such a close abutment is not secured by using a stiff tubular member.

It is the object of the invention to provide a tubular device that renders possible an unobjectionable treatment of the inner surfaces of cavities, namely of the esophagus. By the invention, an inflammation of the mucous membrane of the esophagus is to be effected, which, particularly by repeated treatment, results in a thickening of the esophagus.

To fulfill this object, the invention generally consists in that the device is formed as a tube, is made of flexible, elastic material, especially rubber, and at least on a part of its surface comprises a conductive flexible coating of a biologically safe (inert) material connectable to a source of current via an electric line that is guided within the tubular member under isolation. By the fact that the tubular member consists of a fexible, elastic material, e.g. rubber, an abutment of the tubular member at all areas of the mucous membrance is substantially favorized, and by the surface of the tubular member comprising a flexible coating of conductive, biologically safe material, the flexibility and elasticity of the tubular member itself is not impaired. Thus, the supply of current is largely enhanced at all areas of the mucous membrane. According to the invention, a conductive coating can be deposited by evaporation onto the tubular member as a metallic coating or be brushed onto the tubular member as a matrix containing finely distributed metal, so that a thin coating is obtained in case of vaporizing and a fexible coating in case of embedding the metallic particles into the matrix, which coating does not encroach upon the fexibility of the tubular member. According to the invention, the conductive coating is preferably made of silver which has proved good as a biologically safe material. In accordance with a preferred embodiment of the invention, a layer of silver chloride is arranged on the silver coating. This layer of silver chloride, that, for example, can be produced out of the silver by an electrolytic or a chemical process, effects that polarization phenomena are prevented and that the electric transfer resistance from the silver layer to the mucous membrane is reduced irrespective of the direction of current. Preferably, direct current is used, and in this case, the silver chloride layer has a particularly advantageous result.

According to the invention, at least one connection wire embedded in the conductive coating or positioned at the surface of the latter, which connection wire consists of a biologically safe metal, especially silver, is connected to the electric line guided in the tubular member. The arrangement of the connection wire has the advantage that over the entire length of the conductive coating, the current is supplied to this caoting by this connection wire, because due to this arrangement, the contact resistance between the silver wire and the silver coating is reduced. According to the invention, the connection wire can be laid around the tubular member in coils.

It is essential to the invention that the conductive coating abuts the mucous membrane as closely as possible so as to obtain the effect of the current in all areas of the mucous membrane. This is favorized by the flexibility of the tubular member and the coating. According to a preferred embodiment of the invention, however, the tubular member is expansible within the area of the conductive coating so that by expanding the tubular member the conductive coating is closely pressed on the mucous membrane in all areas. As to this aspect, it is important that in spite of the extension brought about when expanding the tubular member, the electric contact between the metallic particles in the matrix of the coating is maintained. This is achieved, for example, by the metal (especially silver) being embedded in a polymer matrix as a netting of finest wires. A fine netting assures the electric contact of the conductive particles over the entire surface of the coating.

In accordance to another preferred embodiment of the invention, the tubular member comprises an expansible balloon at its free end. When the tubular member is inserted into the esophagus, the balloon arrives within the stomach. After expansion of the balloon, the tubular member can be retracted so far that the expanded balloon pushes against the area where the esophagus enters the stomach. Thereby, the correct position of the tubular member can be controlled, and moreover it is avoided that the tubular member is pulled out of the esophagus during the treatment. Varicous veins exist also within the region of entry of the esophagus into the stomach (cardia). According to the invention, the balloon, too, at its side facing the tubular member, can comprise a coating of silver and the like which can be supplied with current via at least one connection wire. Thereby, also the treatment of such varicose veins appearing within the area of entry of the esophagus into the stomach (cardia) is made possible in the same manner. Preferably, in accordance with the invention, the tubular member is provided at its operating end with a connection for pressurized fluid for expanding the expansible part of the tubular member and the balloon. Generally, water is used as a pressurized fluid.

Only one of the poles can be connectable to the electric line guided within the tubular member, whereas the other pole is connectable to a skin electrode. Thus, the closing of circuit is effected via the conductive coating and via the mucous membrane by the body. However, according to the invention, the arrangement can be such that the conductive coating is divided into fields electrically isolated from each other, with two electric lines being guided within the tubular member which are connected to different poles of the direct current source and one of which respectively is electrically connected to a field or a group of fields. In this case, the current flows via the mucous membrane from one field to the other or from one group of fields to the other group.

The conductive coating can be subdivided into fields electrically isolated from each other, and a separate electric line carried within the tubular member can be assigned to each field.

In a manner per se known, also a tubular device intended for the treatment of the esophagus can comprise a tube running through the balloon and opening out into the stomach, through which tube fluids can be delivered to the stomach or sucked out of it.

In the drawings, the invention is systematically demonstrated with reference to different embodiments.

FIG. 1 shows an embodiment of the tubular device.

FIG. 2 illustrates an embodiment of an expansible tubular device.

The tubular device according to FIG. 1 consists of a flexible tube 1, e.g. made of rubber. Within an area a the tubular member comprises a coating 2 of silver or silver particles enclosed in a matrix, which coating is indicated by hatched lines in the drawing. A connection wire 3 is arranged in coils around coating 2 and electrically connected to it. This connection wire 3 can also be embedded in the matrix of coating 2, thus not immediately touching the mucous membrane. Within tubular member 1, there is arranged an electric wire 3a which connects connection wire 3 to a plug socket 4 at the operating end 5 of the tubular member. Plug socket 4 is connected to a current source 6 the other pole of which is linked to a plug socket 7 of a main electrode 8. The main electrode 8 can be placed upon the chest. At its free end 9, tubular member 1 is provided with an expansible balloon 10 which can be enlarged by pressure water via a pressure water connection (not shown). The tubular member, if it is used for a treatment of the esophagus, is introduced into the stomach via the esophagus so that the expanded balloon 10 precludes the tubular member from slipping out. When the tubular member is extracted, the pressure is taken away from balloon 10.

Another connection 11 for pipes or tubes is provided at operating end 5 of the tubular member. The tubular member tube or a separate tube 12 guided within the tube passes through balloon 10. Fluids can be introduced into the stomach via connection 11, which fluids can enter the stomach through an opening 13, or a fluid can be sucked off.

For example, a tubular device of this type can serve for the treatment of the esophagus of children but as well for the treatment of the esophagus of adults.

In FIG. 2, another embodiment of the tubular device is shown. Area a, which carries the silver coating 2, is expansibly arranged and can be expanded by pressure water. Here too, a connection wire 3 is provided which is embedded in the matrix of silver coating 2. Connecting wire 3 is coiled in such a manner that it can follow the expansion of region a without breaking apart. Connecting wire 3 is connected to a plug socket 4 via a conducting wire (not shown) guided within tubular member 1a, the plug socket being linked to current source 6. The area a provided with the silver coating only has to be as long as the extension of the mucous membrane area to be treated. However, an adjoining area b without a coating can be expanded by water pressure in the same way so as to guarantee a safe hold of the tubular member within the esophagus.

At the free end 9 of tubular member 1a, there is again provided an expansible balloon 14. In the embodiment according to FIG. 2 this balloon 14 at the side 15 facing tubular member 1a comprises a silver coating to which current is supplied via a connection wire 16 again. The coated area 15 of the balloon abuts the wall of the stomach within the entering area of the esophagus (cardia), and thus it is possible to treat varicose veins in this area of the stomach as well. Here, too, connections 17 and 18 are provided through which fluid for the stomach can be supplied via tubular member 1a or tubes 19 guided within tube 1a to a tube 20 which is carried through balloon 14. Exit ports for the fluid are indicated by numeral 21.

The tubular device illustrated by FIG. 1 and 2 is meant for the treatment of the esophagus. However, the tubular device according to the invention can be used for other hollow organs as well, as, for example, for the treatment of hemorrhoids.

We claim:

1. Tubular device for the treatment of the mucous membrane of a hollow organ from an electric current source having a first pole and a second pole, comprising:

a flexible tubular member operable for insertion into sand hollow organ and having on at least a part of its surface a first conductive flexible coating of a biologically safe material and a second conductive flexible coating of a biologically safe material, said first and second conductive coatings being electrically isolated from each other, said first coating being connectable to said first pole of said electric current source via a first isolated electric line, and said second coating being connectable to said second pole of said electric current source via a second isolated electric line, contact means for bringing said first and second conductive coating into contact with said mucous membrane, current means for establishing current flow between said first and second conductive coatings along said mucous membrane, whereby said mucous membrane is electrically stimulated by current flow between said first and second conductive coatings along said mucous membrane to thereby effect an inflamation of said mucous membrane.

2. Tubular device according to claim 1, wherein at least one of said first and second conductive coatings is deposited by evaporation onto the tubular member as a metallic coating.

3. Tubular device according to claim 1, wherein at least one of said first and second conductive coatings is silver.

4. Tubular device according to claim 3, wherein a layer of silver chloride is provided on the silver coating.

5. Tubular device according to claim 1, wherein at least one connection wire made of a biologically safe material is connected to at least one of the first and second isolated electric lines guided within the tubular member.

6. Tubular device according to claim 5, wherein the connection wire is arranged in coils around the tubular member.

7. Tubular device according to claim 5, further comprising means for expanding the tubular member within the area of the first and second conductive coatings.

8. Tubular device according to claim 1, wherein at least one of said first and second conductive coatings is embedded in a polymer matrix as a netting of wires.

9. Tubular device according to claim 1, further comprising an expansible balloon at a first end thereof.

10. Tubular device according to claim 9, wherein the balloon comprises a coating of silver or the like, is provided for supplying current to said coating.

11. Tubular device according to claim 1, further comprising a connection for pressurized fluid for the expansion of the expansible section of the tubular member within the area of the first and second conductive coatings.

12. Tubular device according to claim 1 wherein at least one of said first and second conductive coatings is embedded into the tubular member material.

13. Tubular device according to claim 1 wherein at least one of said first and second conductive coatings is brushed onto the tubular member as a matrix containing finely distributed metal.

14. A device for the medical treatment of a body cavity wall having a mucous membrane, said device comprising:
- a flexible tube operable for insertion into said body cavity, said flexible tube having thereon a first conductive area and a second conductive area, said first and second conductive areas being electrically isolated from each other,
- contact means for bringing said first and second conductive areas into contact with said body cavity wall, and
- current means for establishing a current flow between said first and second conductive areas along said body cavity wall,
- whereby said body cavity wall is electrically stimulated by said current flow to thereby effect an inflamation of said mucous membrane.

15. A device for the medical treatment of a body cavity wall having a mucous membrane, said device comprising:
- a flexible tube operable for insertion into said body cavity, said flexible tube having thereon a first conductive area and a second conductive area, said first and second conductive areas being electrically isolated from each other,
- contact means for bringing said first and second conductive areas into contact with said body cavity wall,
- a current source having a first pole and a second pole,
- first connection means for electrically connecting said first conductive area to said first pole,
- second connection means for electrically connecting said second conductive area to said second pole,
- whereby a current flow is established along the body cavity wall between the first and second conductive areas to thereby electrically stimulate the body cavity wall to thereby effect an inflamation of said mucous membrane.

16. A device as in claim 14 wherein said contact means comprises an inflatable balloon.

17. A method for the medical treatment of a body cavity wall having a mucous membrane by a flexible tube having thereon a first conductive area and a second conductive area, said first and second conductive areas being electrically isolated from each other, said method comprising the steps of:
- inserting said flexible tube into said body cavity,
- bringing said first and second conductive areas into contact with said body cavity wall, and
- establishing a current flow between said first and second conductive areas along said body cavity wall,
- whereby said body cavity wall is electrically stimulated by said current flow to thereby effect an inflamation of said mucous membrane.

* * * * *